United States Patent [19]  
Georgiev et al.

[11] Patent Number: 4,705,891  
[45] Date of Patent: Nov. 10, 1987

[54] SUBSTITUTED α-[2'-TRICYCLO[3.3.1.1³,⁷]DECYLIDENE]-BENZENEACETIC ACID DERIVATIVES

[75] Inventors: Vassil S. Georgiev, Rochester; George B. Mullen, Avon, both of N.Y.

[73] Assignee: Pennwalt Corporation, Philadelphia, Pa.

[21] Appl. No.: 867,130

[22] Filed: May 27, 1986

[51] Int. Cl.$^4$ ............................................. C07C 63/33
[52] U.S. Cl. ................................... 562/491; 514/569; 562/466; 560/101; 560/57; 560/56
[58] Field of Search .................. 562/491; 560/101, 56, 560/57

[56] References Cited  
U.S. PATENT DOCUMENTS  
3,624,126 11/1971 Narayanan ...................... 260/468 B OTHER PUBLICATIONS  
Aigami et al., "Biologically Active Polycycloalkanes.1 Antivirial Adamantane Derivatives," J. Med. Chem. 18, 713–721 (1975).  
CA 83:96537t, Inst. Org. Khim., Danilenko et al., "Bacteriostatic Effect of Adamantanecarboxylic Acids".

Primary Examiner—Paul J. Killos  
Attorney, Agent, or Firm—David M. Bunnell

[57] ABSTRACT

Substituted α-[2'-tricyclo[3.3.1.1³,⁷]decylidene]-benzeneacetic acid derivatives of the formula:

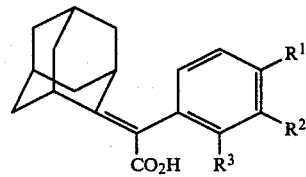

where the $R^1$, $R^2$ and $R^3$ substituents are independently selected from hydrogen, lower alkyl, lower alkoxy, halogen and trifluoromethane, provided that at least one of such substituents is hydrogen have antihypoxia, anticonvulsant and/or antiparkinson activities.

7 Claims, No Drawings

SUBSTITUTED α-[2'-TRICYCLO[3.3.1.1³,⁷]DECYLIDENE]-BENZENEACETIC ACID DERIVATIVES

BACKGROUND OF THE INVENTION

In a concurrently filed commonly assigned application entitled, "Substituted α-[2'-Tricyclo]3.3.1.1$^{3,7}$-]decylidene benzeneacetonitrile Derivatives", whose teachings are hereby incorporated by reference, substituted α-[2'tricyclo [3.3.1.1$^{3,7}$]decylidene]benzeneacetonitrile derivatives which have antihypoxia activity are described. We have prepared related benzeneacetic acid derivatives which possess antihypoxia, antiparkinson and/or anticonvulsant activities, that is they either protect warm-blooded animals from the effects of oxygen deprivation, reduce pentylenetetrazole- or electric shock induced seizures, or reduce N-carbamoyl-2-(2,6-dichlorophenyl)acetamide hydrochloride-induced tremors.

BRIEF SUMMARY OF THE INVENTION

In accordance with this invention there are provided compounds of the formula:

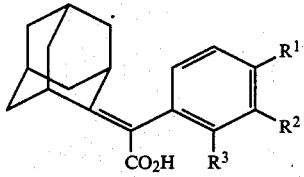

where the $R^1$, $R^2$ and $R^3$ substituents are independently selected from hydrogen, lower alkyl, lower alkoxy, halogen and trifluoromethane provided that at least one of such substituents is hydrogen.

DETAILED DESCRIPTION

As used herein the terms "lower alkyl" and "lower alkoxy" refer to straight and branched chain alkylene groups having 1 to 4 carbons and "halogen" refers to chlorine, bromine, iodine and fluorine (preferably chlorine).

As described in the following Examples, the compounds of the invention can be prepared from the corresponding α-[2'-tricyclo[3.3.1.1$^{3,7}$]decylidene]benzeneacetonitrile derivatives 3 which are described in the above mentioned copending application and which can be obtained by the condensation of 2-adamantanone 1 with the appropriate phenylacetonitrile 2 in tetrahydrofuran solution and in the presence of potassium tert-butoxide. Sequential treatment of the benzeneacetonitrile derivatives with diisobutylaluminum hydride to provide the aldehyde 4, and then with sulfamic acid-sodium chlorite provides the title α-[2'-tricyclo[3.3.1.1$^{3,7}$]decylidene]benzeneacetic acids 5. The reaction scheme is as follows:

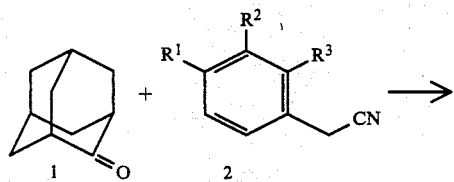

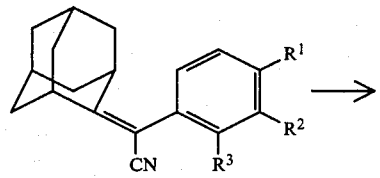

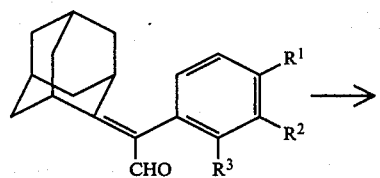

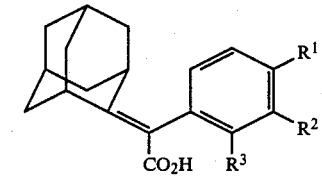

EXAMPLE 1

α-[2'-Tricyclo[3.3.1.1$^{3,7}$]decylidene]benzeneacetic Acid

A solution of 10.0 g (0.04 mol) of α-[2'-tricyclo[3.3.1.1$^{3,7}$]decylidene]benzeneacetonitrile (3, $R^1=R^2=R^3=H$) in 50 ml methylene chloride was added over 30 min to 55 ml of a 1M solution of diisobutylaluminum hydride in methylene chloride under a nitrogen atmosphere. The reaction was stirred for 3 hours, then cooled in an ice bath and quenched by dropwise addition of 60 ml of 6N sulfuric acid, followed by addition of water and methylene chloride. The organic layer was washed sequentially with water, saturated aqueous sodium bicarbonate, and saturated aqueous sodium chloride, then dried over magnesium sulfate. Removal of the solvent in vacuo yielded the corresponding aldehyde (4, $R^1=R^2=R^3=H$) as an unstable oil. Without further purification, the latter was dissolved in 30 ml of tetrahydrofuran and 400 ml of potassium biphthalate buffer (pH 4.0) was added with vigorous stirring followed by 5.04 g (1.3 equivalent) of sulfamic acid and 6.68 g (1.3 equivalent) of sodium chlorite dihydrate. The yellow reaction mixture was stirred for 2 hours at room temperature, then water and ether were added and the two layers were separated. The organic extract was washed with saturated aqueous sodium chloride and dried over magnesium sulfate. Crystallization from ethyl acetate provided 8.57 g of the product acid (5, $R^1=R^2=R^3=H$). Mp 182°–186° C. Anal. Calcd. for $C_{18}H_{20}O_2$; C, 80.56; H. 7.51. Found: C, 80.18; H, 7.38.

EXAMPLE 2

3-Chloro-α-[2'-tricyclo[3.3.1.1$^{3,7}$]decylidene]benzeneacetic Acid

The title compound (5, $R^1=R^3=H$, $R^2=Cl$) was prepared by a method similar to that described in Example 1 from 3-chloro-α-[2'-tricyclo[3.3.1.1$^{3,7}$-

]decylidene]benzeneacetonitrile (3, $R^1=R^3=H$, $R^2=Cl$) via the corresponding aldehyde (4, $R^1=R^3=H$, $R^2=Cl$). The product acid has a melting point of 185° C. (methanol). Anal. Calcd. for $C_{18}H_{19}ClO_2$: C, 71.40; H, 6.32; Cl, 11.71. Found: C, 71.00; H, 6.33; Cl, 11.64.

EXAMPLE 3

4-Methyl-α-[2'-tricyclo[3.3.1.1$^{3,7}$]decylidene]benzeneacetic Acid

The title compound (5, $R^1=CH_3$, $R^2=R^3=H$) was prepared by a method similar to that described in Example 1 from 4-methyl-α-[2'-tricyclo[3.3.1.1$^{3,7}$]decylidene]benzeneacetonitrile (3, $R^1=CH_3$, $R^2=R^3=H$), via the corresponding aldehyde (4, $R^1=CH_3$, $R^2=R^3=H$). The product acid has a melting point of 201°–202° C. (methanol). Anal. Calcd. for $C_{19}H_{22}O_2$: C, 80.82; H, 7.85. Found: C, 81.02; H, 7.81.

EXAMPLE 4

2-Methyl-α-[2'-tricyclo[3.3.1.1$^{3,7}$]decylidene]benzeneacetic Acid

The title compound (5, $R^1=R^2=H$, $R^3=CH_3$) was prepared by a method similar to that described in Example 1 from 2-methyl-α-[2'-tricyclo[3.3.1.1$^{3,7}$]decylidene]benzeneacetonitrile (3, $R^1=R^2=H$, $R^3=CH_3$) via the corresponding aldehyde (4, $R^1=R^2=H$, $R^3=CH_3$). The product acid has a melting point of 120° C. (methanol). Anal. Calcd. for $C_{19}H_{22}O_2$: C, 80.82; H, 7.85. Found: C, 80.82: H, 7.87.

EXAMPLE 5

3-Trifluoromethyl-α-[2'-tricyclo[3.3.1.1$^{3,7}$]decylidene]benzeneacetic Acid

The title compound (5, $R^1=R^3=H$, $R^2=CF_3$) was prepared by a method similar to that described in Example 1 from 3-trifluoromethyl-α-[2'-tricyclo[3.3.1.1$^{3,7}$]decylidene]benzeneacetonitrile (3, $R^1=R^3=H$, $R^2=CF_3$) via the corresponding aldehyde (4, $R^1=R^3=H$, $R^2=CF_3$). The product acid has a melting point of 198°–200° C. (methanol). Anal. Calcd. for $C_{19}H_{19}F_3O_2$: C. 67.85; H, 5.69; F, 16.95. Found: C, 67.90; H, 5.93; F, 16.79.

EXAMPLE 6

4-Chloro-α-[2'-tricyclo[3.3.1.1$^{3,7}$]decylidene]benzeneacetic Acid

The title compound (5, $R^1=Cl$, $R^2=R^3=H$) was prepared by a method similar to that described in Example 1 from 4-chloro-α-[2'-tricyclo[3.3.1.1$^{3,7}$]decylidene]benzeneacetonitrile (3, $R^1=Cl$, $R^2=R^3=H$). The product has a melting point of 218°–219° C. (methanol). Anal. Calcd. for $C_{18}H_{19}ClO_2$: C, 71.40; H, 6.32; Cl, 11.71. Found: C, 71.19; H, 6.53; Cl, 11.18.

Compounds possessing useful antihypoxia activity extend the lifetime of animals exposed to a hypoxic environment. This activity is conveniently measured in mice. Groups of mice are tested at various times after the intraperitoneal administration of the test compound dissolved in saline in dosages of 1 to 100 mg/kg of mouse weight. The animals' survival time in a hypoxic environment (96% nitrogen and 4% oxygen) is recorded. A statistical comparison (Wilcoxon Rank sum) is made between coincident vehicle treated animals and the experimental group. The compounds of Examples 1, and 4 to 6 were tested at the 100 mg/kg dosage level and were found active.

The evaluation of the anti-convulsant activity of drugs is based mainly on their ability to block the pentylenetetrazole(PTZ)- and/or electric shock-induced convulsions. In general, compounds which protect animals against pentylenetetrazole-induced seizures are useful in the treatment of petit mal epilepsy, and drugs which protect animals against electric shock-induced convulsions are effective in the treatment of grand mal and focal seizures. Compounds possessing broader activity which protect animals against both forms of induced seizures may be useful in the treatment of adult petit mal and psychomotor epilepsies.

In the PTZ-induced seizure test two groups of 5 mice each are administered the test compound at ¼ of the LD50 dose or vehicle intraperitonially (i.p.). Thirty minutes later each mouse is administered PTZ, 150 mg/kg i.p. The mice are housed by groups in plastic cages. The animals are observed for 15 minutes immediately following PTZ administration. Alternation of the convulsive pattern such as delayed onset of convulsions, changes in the type of convulsions and prevention of convulsions are noted. The number of survivors 15 minutes after PTZ administration is recorded.

The dose of PTZ used as a convulsive challenge is higher than the LD100 dose, therefore, the number of surviving mice 15 minutes post PTZ can be used as an index of anticonvulsive activity. Active compounds are considered as those that protect 3 or more mice. Most compounds which afford protection against death also delay and moderate or prevent PTZ-induced seizures. The seizure pattern of untreated mice (controls) is: (1) initial twitching, (2) a more severe generalized jerking of the body usually accompanied by a squeak which is followed immediately by (3) frank clonic convulsion which lead to tonic convulsions with tonic extension of the hind limbs. The compounds of Examples 1 to 3 were found active at a dosages 225, 250 and 350 mg/kg of mouse weight respectively.

In the electric shock test, mice are subjected to a shock of 50 mA for 0.2 seconds applied through saline-wetted corneal electrodes. The control group is tested similarly. Untreated mice subjected to electric shock exhibit a typical seizure pattern. Tonic flexion occurs immediately after shock. This changes to tonic extension (hind limb) with 0.5 to 2 seconds and then into generalized clonic convulsions, followed by depression and recovery. The criterion for drug activity is prevention of hind limb tonic extension in 3 or more mice. Some compounds will prevent the tonic phase of the seizure entirely (flexion and extension). The compound of Example 6 was found to be active at a dosage of 350 mg/kg of mouse weight.

We claim:

1. A compound of the formula:

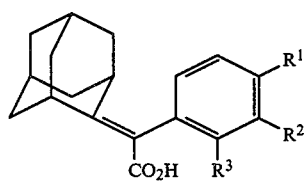

where the $R^1$, $R^2$ and $R^3$ substituents are independently selected from hydrogen, lower alkyl, lower alkoxy, halogen and trifluoromethane, provided that at least one of such substituents is hydrogen.

2. A compound according to claim 1 wherein the compound is α-[2'-tricyclo[3.3.1.1$^{3,7}$]decylidene]benzeneacetic acid.

3. A compound according to claim 1 wherein the compound is 3-chloro-α-[2'-tricyclo[3.3.1.1$^{3,7}$]decylidene]benzeneacetic acid.

4. A compound according to claim 1 wherein the compound is 4-methyl-α-[2'-tricyclo[3.3.1.1$^{3,7}$]decylidene]benzeneacetic acid.

5. A compound according to claim 1 wherein the compound is 2-methyl-α-[2'-tricyclo[3.3.1.1$^{3,7}$]decylidene]benzeneacetic acid.

6. A compound according to claim 1 wherein the compound is 3-trifluoromethyl-α-[2'-tricyclo[3.3.1.1$^{3,7}$]decylidene]benzeneacetic acid.

7. A compound according to claim 1 wherein the compound is 4-chloro-α-[2'-tricyclo[3.3.1.1$^{3,7}$]decylidene]benzeneacetic acid.

* * * * *